United States Patent
Akiva

(10) Patent No.: US 6,205,346 B1
(45) Date of Patent: Mar. 20, 2001

(54) ELECTRODES APRON FOR ECG

(75) Inventor: Sharon Akiva, Kiryat Tivon (IL)

(73) Assignee: Tapuz Medical Technology, Ltd., Mobile Post Jordan Valley (IL)

( * ) Notice: Subject to any disclaimer, the term of this patent is extended or adjusted under 35 U.S.C. 154(b) by 0 days.

(21) Appl. No.: 09/051,727

(22) PCT Filed: Oct. 17, 1996

(86) PCT No.: PCT/IL96/00128

§ 371 Date: Sep. 10, 1998

§ 102(e) Date: Sep. 10, 1998

(87) PCT Pub. No.: WO97/14346

PCT Pub. Date: Apr. 24, 1997

(30) Foreign Application Priority Data

Oct. 19, 1995 (IL) .................................................. 115674

(51) Int. Cl.[7] .......................................................... A61B 5/04
(52) U.S. Cl. ........................ 600/388; 600/382; 600/390; 600/393
(58) Field of Search .................................. 600/372–390, 600/509; 607/149, 152

(56) References Cited

U.S. PATENT DOCUMENTS

| | | | |
|---|---|---|---|
| 3,409,077 | * 11/1968 | Durie | 600/509 |
| 4,202,344 | * 5/1980 | Mills et al. | 600/382 |
| 4,381,012 | * 4/1983 | Russek | 600/382 |
| 4,763,660 | 8/1988 | Kroll et al. | |
| 5,224,479 | 7/1993 | Sekine . | |
| 5,301,678 | 4/1994 | Watson et al. . | |
| 5,445,149 | * 8/1995 | Rotolo et al. | 128/644 |
| 5,471,983 | 12/1995 | Magnus . | |
| 5,685,303 | * 11/1997 | Rollman et al. | 600/390 |
| 5,865,740 | * 2/1999 | Kelly et al. | 600/382 |

FOREIGN PATENT DOCUMENTS

| | | | |
|---|---|---|---|
| 0159434 | * 10/1985 | (EP) | 600/390 |
| 94/17729 | 8/1994 | (WO) . | |

* cited by examiner

*Primary Examiner*—Linda C. M. Dvorak
*Assistant Examiner*—David M. Ruddy
(74) *Attorney, Agent, or Firm*—Lowe Hauptman Gopstein Gilman & Berner

(57) ABSTRACT

The present invention relates to an electrodes apron for ECG which is comprised of an apron cast from flexible material to be placed over the chest of the patient, ten electrodes inlaid within the apron in predetermined places wherein six of the said electrodes are located at predetermined distances between the ribs, two under each shoulder and two at both sides of the stomach. Either curved or spiraled conductors are cast within flexible material and each conductor is connected to an electrode. A multiple-pronged cable feeds each of the conductors and includes a connector for connecting the apron to any standard ECG measuring device. The apron also has straps and a belt for tightening the apron on the body of the patient, locating the electrodes of the apron in their required locations for ECG tests.

Another preferred embodiment of the present invention is an electrodes apron having two bracelets for attaching to the arms of the patient. Instead of straps for tying, the two bracelets on both sides of the apron are attached to the arms of the patient and when the arms of the patient are brought to their regular position parallel to the body, the apron is tightened over the chest of the patient.

7 Claims, 1 Drawing Sheet

ELECTRODES APRON FOR ECG

FIELD OF THE INVENTION

The present invention relates to the field of accessories used in devices for medical testing. More specifically, the present invention relates to an electrodes apron for use in electrocardiogram (hereinafter called ECG) medical testing.

BACKGROUND ART

An ECG test is a test which is performed by means of an appropriate testing device. The device measures the potential differences between various selected points on the body of a person to be examined (hereinafter called "patient"). These potential differences mirror the electronic activities of the heart muscle. The measurement is done by way of attaching electrodes to the body of a patient in predetermined places. These electrodes then transfer the electronic information to the testing device. The electrodes are placed around the heart at points between the patient's ribs, known as points V1 to V5, two are attached on the patients arms and two are attached on the patient's legs.

In the present, well known ECG tests, 10 electrodes are attached to the patient's body. In order to attach the electrodes to the body of the patient, disposable electrodes are attached with special glue or with suction buttons which cause discomfort to the patient. Furthermore, a special gel is spread over the attachment points in order to improve electrical conductivity. When the patient is a male, it is sometimes necessary to shave off hair at the point of attachment.

The present situation in which ten separate electrodes are attached to the patient, is awkward because of the use of ten separate conductors, which have a tendency to interfere with each other, and because of the need to glue them to the body of the patient. Discomfort is also caused because of the need to use suction buttons, or to shave the hair prior to placing the conductors on the patients body.

The placement of the electrodes on the patients body requires experience and anatomical knowledge which is not always found among the medical staff. As a result, the electrodes are improperly positioned. When the attachment to the body is not accurate, electrical noise is caused together with disruptions of electrical conductivity. These occurrences cause difficulty in interpreting the data received.

SUMMARY OF THE INVENTION

The present invention relates to an electrodes apron for ECG testing having two bracelets for attaching to the arms of the patient (hereinafter called electrode bracelet apron), so that when the arms of the patient are brought to their regular position parallel to the body, the apron is tightened over the chest of the patient. The electrodes apron for ECG testing of the present invention is comprised of an apron cast from flexible material to be placed over the chest of the patient, ten electrodes inlaid within the apron in predetermined places wherein six of the said electrodes are located at predetermined distances between the patient's ribs, two on each arm of the patient and two at both sides of the patient's stomach. Either curved or spiraled conductors are cast within flexible material and each conductor is connected to an electrode. A multiple-pronged cable feeds each of the conductors and includes a connector for connecting the apron to a measuring device. The two electrodes positioned on the two sides of the stomach are those placed on the legs in the prior art methods.

The apron of the present invention has several advantages. The electrode bracelets apron enables quick wearing of the apron, particularly in emergency situations, since there is no need to bring straps around the back or the neck. Attaching the bracelets to the arms of the patient and straightening the patient's arms so they are parallel with the patient's body, causes the apron to tighten over the patient's chest and the electrodes to be placed in the required spots. It is possible to immediately connect the connector to the testing device and to receive results.

Furthermore, it is possible to connect the electrodes bracelet apron without completely undressing the patient but by raising the patient's shirt and placing the apron under the shirt or bra.

BRIEF DESCRIPTION OF THE DRAWING

The bracelets can be made from metal, thus the bracelets are used as left and right arm electrodes positioning them most accurately on the arms.

The present invention is described in detail by FIGS. 1 and 2. These drawings are not intended to limit the scope of the invention and are solely for purposes of clarification and description.

DETAILED DESCRIPTION OF THE DRAWING

Figure 1:
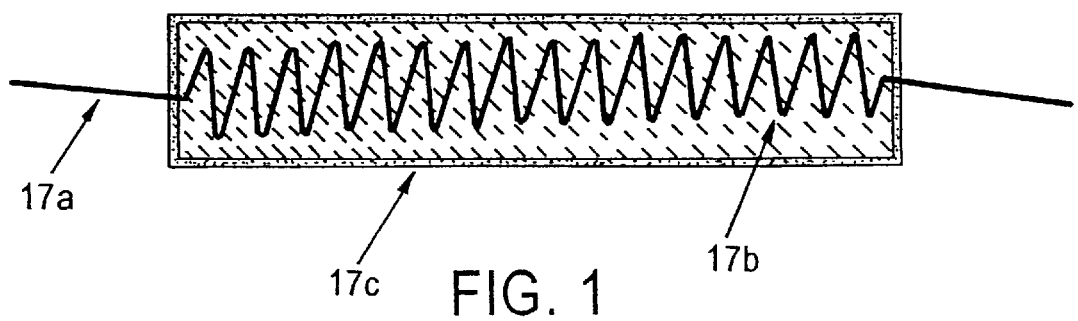

FIG. 1 describes the conductors in the apron.

Figure 2:
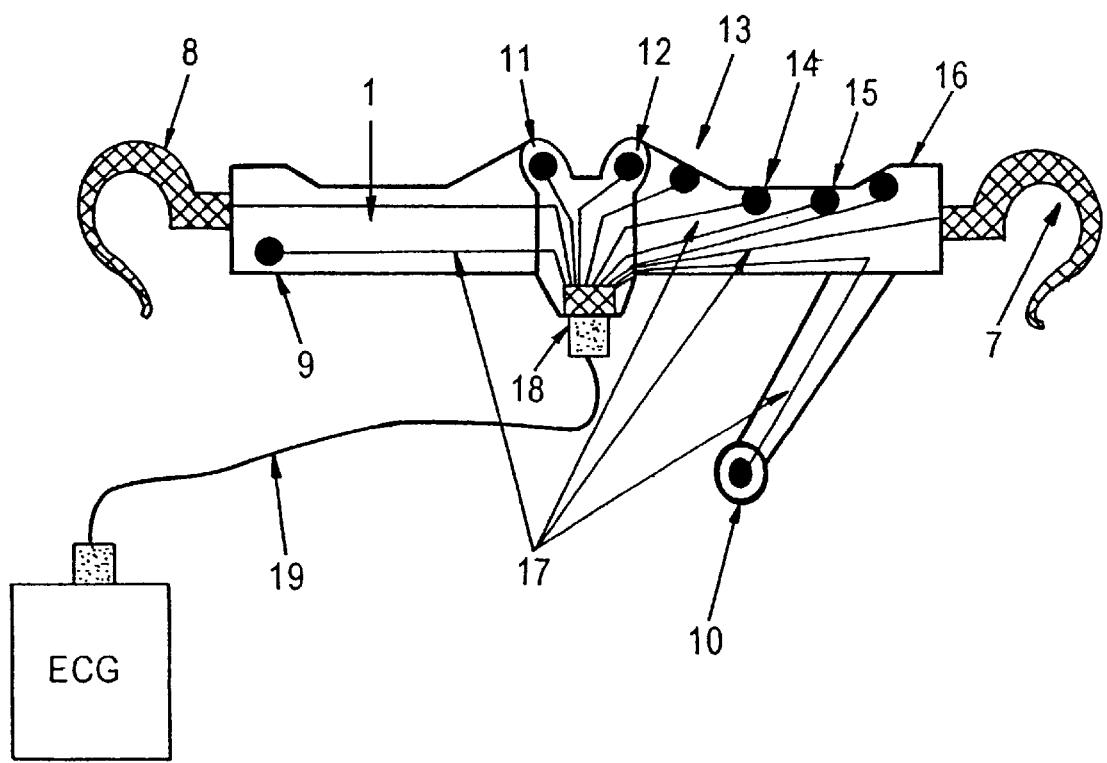

FIG. 2 describes a frontal view of the electrode bracelets apron.

FIG. 1 illustrates the conductor (17a) with its curvature (17b) within an envelope (17c) cast from flexible material such as rubber. It is possible to tighten the conductor, up to a certain limit, together with the cased envelope, without over-tightening or causing damage to the conductor.

FIG. 2 describes a frontal view of the electrodes bracelets apron, the apron is comprised of the apron body (1) made from flexible material and capable of being tightened, two bracelets (7) and (8) on the two sides of the apron for the attachment to the arms of the patient. Together with the straightening of the arms of the patient in parallel with the patient's body, the apron is tightened over the chest of the patient. These two bracelets serve, at the same time, also as the right arm and left arm electrodes. The additional electrodes are located within the cast apron as follows electrodes (9) and (10) provide the right leg and left leg electrodes and six additional electrodes, (11), (12), (13), (14), (15) and (16) provide the pericardial electrodes v1 to v6.

From each electrode emerges a coiled, spiral or zig-zag shaped conductor (17) which is cast within flexible material such that it is capable of tightening the conductor without damage being caused to the conductor. The conductors are connected to a connector (18). A suitable multi-pronged cable (19) connects the connector to any standard ECG device.

For conducting an ECG examination, the bracelets are attached to the patient's arms, and the arms are pulled to the side of the body. Thus the apron is tightened to the chest and by connecting the apron to the measuring device, a full 12 lead ECG examination is performed within seconds.

In accordance with this invention, the apron is worn on the body of the patient and tightened by means of the bracelets. As a result, there is no need for suction buttons, gel, or shaving hair. The electrodes are located at the appropriate positions required for testing and the data received from those very same locations is in a manner which assists in the quality of the examination.

The apron is tightened according to need and is adaptable to the body of the patient. The electrodes are positioned according to tension in the anatomically accurate places required for examination and the distance between them changes proportionally according to the size of the patient's body. The structure of the apron enables medical testing of both males and females with no need for different aprons.

At the time of tightening, no damage is caused to the conductors because they are protected by their special structure, as described in the figures.

Wearing an apron, according to the present invention, instead of positioning, one by one, ten electrodes, makes the apron simple to wear and enables the rapid performance of an ECG test, which is of substantial importance in times of emergencies.

What is claimed is:

1. An electrodes apron for use in ECG testing of a patient, comprising said apron made of a flexible and stretchable material, and including two arm bracelets for grasping the arms of the patient, said bracelets connected to the apron for stretching the apron over the patient's chest with the straightening of the patient's arms, a plurality of electrodes disposed on the apron so that stretching of the apron will locate the electrodes in predetermined locations, a plurality of conductors adapted to be connected to a respective electrode, and a cable connected at one end thereof to each conductor and at another end thereof adapted to be connected to an ECG measuring device.

2. An electrodes apron for use in ECG testing according to claim 1, wherein ten electrodes are inlaid within the apron, six electrodes adapted to fit in spaces between the ribs of the patient, two in the arm bracelets and two adapted to fit at both sides of the stomach of the patient.

3. An electrodes apron for use in ECG testing according to claim 1, wherein the conductors are coiled, curved or spiral.

4. An electrodes apron for use in ECG testing according to claim 1, wherein the arm bracelets are made of metal and the arm bracelets are for use as two additional arm electrodes.

5. An electrodes apron for use in ECG testing according to claim 1, wherein the apron is a cast flexible and stretchable material.

6. An electrodes apron for use in ECG testing according to claim 1, wherein the conductors are located within the apron material.

7. A method of using an electrodes apron to perform ECG testing, the electrodes apron made of a flexible and stretchable material, the apron including two arm bracelets, a plurality of electrodes disposed on the apron, a plurality of conductors each adapted to be connected to a respective electrode, a cable connected at one end thereof to each conductor and at another end thereof adapted to be connected to an ECG measuring device, the method comprising the steps of:

positioning the apron across the patient's chest;

placing the arm bracelets on the arms of the patient;

positioning the apron electrodes by straightening the arms of the patient parallel to the patient's body; and, connecting the cable to the ECG measuring device.

* * * * *